United States Patent [19]

Richter et al.

[11] 4,207,326

[45] Jun. 10, 1980

[54] ANTIMICROBIAL QUATERNARY PYRAZOLE DERIVATIVES

[75] Inventors: Carl Richter; Georg Feth, both of Schaffhausen, Switzerland

[73] Assignee: Cilag-Chemie A.G., Schaffhausen, Switzerland

[21] Appl. No.: 41,130

[22] Filed: May 21, 1979

[51] Int. Cl.$^2$ .............. C07D 231/12; A61K 31/415; A01N 9/22
[52] U.S. Cl. .......................... 424/273 P; 548/373; 548/378
[58] Field of Search .................. 548/373, 378; 424/273 P

[56] References Cited

U.S. PATENT DOCUMENTS

| | | | |
|---|---|---|---|
| 3,818,096 | 6/1974 | Sherlock | 424/273 P |
| 3,907,825 | 9/1975 | Cross et al. | 548/373 |
| 3,929,451 | 12/1975 | Cross et al. | 548/373 |
| 3,930,011 | 12/1975 | Walworth | 424/273 P |
| 3,966,954 | 6/1976 | Walworth | 424/273 P |
| 4,003,732 | 1/1977 | Cross | 71/92 |
| 4,017,298 | 4/1977 | Cross et al. | 548/373 |

OTHER PUBLICATIONS

Grandberg, Chem. Abst., 1965, vol. 63, p. 8339e.

*Primary Examiner*—Alan L. Rotman
*Assistant Examiner*—Natalia Harkaway
*Attorney, Agent, or Firm*—Benjamin F. Lambert

[57] ABSTRACT

Quaternary N-alkyl pyrazole derivatives and their method of preparation are described. The pyrazole derivatives are useful as antimicrobial agents.

35 Claims, No Drawings

ANTIMICROBIAL QUATERNARY PYRAZOLE DERIVATIVES

BACKGROUND OF THE INVENTION

A number of quaternary pyrazole derivatives are reported in the literature, typical of which are those herbicidal or hypoglycemic agents found in the following United States patents:
U.S. Pat. No. 3,818,096;
U.S. Pat. No. 3,907,825;
U.S. Pat. No. 3,929,451;
U.S. Pat. No. 4,003,732; and
U.S. Pat. No. 4,017,298.

The compounds of the present invention differ from such prior art compounds by having a long-chain alkyl ($C_{10}$–$C_{18}$) in the 1-position of the pyrazole ring and by their antimicrobial activity.

Although antifungal pyrazolium compounds are reported in U.S. Pat. No. 3,966,954, such compounds are necessarily limited to methyl in said 1-position.

DESCRIPTION OF THE PREFERRED EMBODIMENTS

This invention relates to a novel class of quaternary pyrazole derivatives and more particularly to pyrazolium salts with a long-chain alkyl function in the 1-position having the formula:

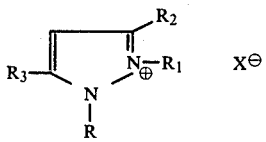

wherein:
R is an alkyl having from 10 to 18 carbons with at least 10 carbons in its longest chain;
$R_1$ is a member selected from the group consisting of lower alkyl, $C_3$–$C_5$ alkenyl, benzyl, nitrobenzyl, halobenzyl and dihalobenzyl;
$R_2$ is a member selected from the group consisting of hydrogen and methyl;
$R_3$ is a member selected from the group consisting of hydrogen and methyl; and
X is an anion.

The term "lower" as used herein is meant to signify from 1 to about 5 carbons in the so-modified term; and the term "halo" is generic to halogens of atomic weight less than 127, i.e., chloro, bromo, fluoro and iodo, with chloro being most preferred. Typical $C_3$–$C_5$ alkenyls include allyl, methallyl, 2-pentenyl and the like.

Illustrative of the anions which are suitable for use in the present invention are those derived from a mineral acid such as a halide, e.g., chloride, bromide and iodide; sulfate; nitrate; phosphate and the like. Other typical anions include hydrogen sulfate; methyl sulfate; ethyl sulfate; sodium sulfate; magnesium phosphate; sodium hydrogen phosphate; benzene sulfonate; alkyl ($C_1$–$C_4$) benzene sulfonate, preferably p-toluene sulfonate; alkoxy ($C_1$–$C_4$) benzene sulfonate; and the like. The most preferred anions are methyl sulfate (i.e., methosulfate), ethyl sulfate (i.e., ethosulfate), chloride, bromide, phosphate and p-toluene sulfonate.

Due to the inherent resonance within the pyrazolium ring, it is evident that the compounds of formula (I) can be depicted in a resonant form other than as shown. In this specification and in the claims, formula (I) is intended to include all resonance forms thereof.

The preferred compounds of formula (I) are those wherein R is alkyl having from 12 to 16 carbons with at least 10 carbons in its longest chain.

The quaternary compounds of formula (I) are conveniently prepared either by alkylation of a pyrazole having the formula:

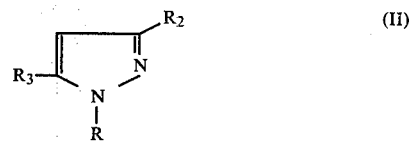

wherein R, $R_2$ and $R_3$ are as previously described, with an appropriate alkylating agent, or, often more conveniently, by standard anion exchange techniques.

The pyrazole alkylation is usually carried out in the presence of an inert organic solvent at elevated temperatures sufficient to enhance the rate of reaction, generally between 50° C. and 200° C. and, preferably, between 90° C. and 120° C. or under reflux conditions. Illustrative of the solvents which may be employed in the alkylation reaction are aromatic hydrocarbons, e.g., toluene, xylene and chlorobenzene; ketones having 4 to 7 carbons such as methyl isobutyl ketone (MIBK) and methyl butyl ketone (MBK); ethyl acetate; sulfolane (liquefied: m.p. about 25°–27° C.); dimethyl formamide (DMF); cyclic ethers, e.g., dioxane and tetrahydrofuran (THF); acetonitrile; and the like.

Exemplary of the alkylating agents are lower alkyl halides, di-lower alkyl sulfates, lower alkyl phosphates, lower alkyl hydrogen sulfates, lower alkyl toluene sulfonates, lower alkenyl halides, benzyl and appropriately substituted benzyl halides, and the like, which alkylating agents are suitable for the substitution of an $R_1$ group in the 2-position of the pyrazole ring.

While equimolar amounts of pyrrole precursor (II) and alkylating agent can be employed, it is a good practice to employ a slight excess of alkylating agent to insure completion of the reaction, for example, from 1:1 to 1:1.5, respectively.

Compounds of formula (I) having a particular anion $X^-$, which may be difficult to obtain by an alkylation procedure or are so obtainable in low yields or in an impure state, may advantageously be prepared by conventional anion exchange methodology from previously prepared formula (I) compounds having a different pyrazolium anion. The exchange may be affected by treating the initially formed salt with a suitable ion exchange resin, for example, a strongly basic anion exchanger such as a Dowex 1-x8, Amberlite IRA-401 and the like. Illustrative exchangers employ quaternary ammonium salts. Where the resin is supplied as the salt of an anion other than that desired, it is pretreated with an aqueous solution of a salt of the desired anion. For example, if the resin is supplied as a quaternary ammonium chloride and it is desired to produce a pyrazolium bromide, one would pretreat the resin with hydrobromic acid.

Since quaternization by alkylation is technically much easier with alkylating agents such as, for example, dialkyl sulfates, than with, for example, methyl chloride which is volatile at normal temperatures, it is particularly advantageous to obtain the quaternary halides of formula (I) by means of ion exchange chromatography.

The methodology involved in the aforementioned alkylation reactions and anion exchange techniques is amply provided for in the literature such as, for example, the prior art patent references alluded to at the beginning of this specification and such is incorporated herein.

The formula (II) precursors, some of which are described in the literature, are obtainable by the reaction of pyrazole or an appropriate derivative thereof, for example, 3-methylpyrazole or 3,5-dimethylpyrazole, with an appropriate long-chain alkyl halide as described, for example, in Bull Soc. Chim. France 1976, 1861–4 and in Chim. Geterotsikl. Soedin., Akad. Nauk, Latv. SSR 1965, (2), 279–83 [Chem. Abstracts 63, 8339e–g (1965)].

The compounds of formula (1) are effective antimicrobial agents which are particularly useful in combatting such microorganisms as bacteria, yeasts, fungi and algae as demonstrated by their broad spectrum of action against same. As used herein, the term "antifungal" embraces the term "antimycotic". Typical of the microorganisms susceptible of the antimicrobial activity of the subject compounds are the following:

A. Bacteria:

1. Staphylococcus aureus (S. aureus)
2. Streptococcus pyogenes (S. pyogenes)
3. Escherichia coli (E. coli)
4. Proteus mirabilis (P. mirabilis)
5. Pseudomonas aeruginosa (P. aeruginosa)

B. Yeasts:

6. Candida albicans (C. albicans)
7. Candida tropicalis (C. tropicalis)
8. Cryptococcus neoformans (C. neoformans)

C. Fungi:

9. Absidia corymbifera (A. corymbifera)
10. Aspergillus fimigatus (A. fumigatus)
11. Sporotrichon schenkii (S. schenkii)
12. Trichophyton rubrum (T. rubrum)
13. Trichophyton mentagrophytes (T. mentagrophytes)
14. Microsporum canis (M. canis)
15. Phialophore verrucosa (P. verrucosa)

The antimicrobial activity was determined by inoculation of the test microorganism into suitable growth media containing solutions of the compounds at concentrations of 100, 50, 10, 5, 1.0, 0.5 and 0.1 µg/ml. The reference antibiotics used were Gentamicin for the antibacterial tests and Amphotericin B for the antimycotic and antifungal tests. After incubation the antimicrobial activity was recorded as the Minimal Inhibitory Concentration (M.I.C.), i.e., the lowest concentration preventing macroscopically visible growth, for each test compound against each organism.

PREPARATION OF TEST SOLUTIONS

An initial solution of each formula (I) compound to be tested in sterile distilled water was prepared at a concentration of 1000 µg/ml. With appropriate dilutions using sterile distilled water, additional solutions were prepared at concentrations of 500, 100, 50, 10, 5 and 1 µg/ml.

MICROBIAL STRAINS AND PREPARATION OF INOCULA (a) Bacteria

The following strains were obtained from the National Collection of Type Cultures, Colindale Avenue, London NW9 5HT as freeze-dried cultures:

| | |
|---|---|
| S. pyrogenes | NCTC 8198 |
| P. mirabilis | NCTC 8559 |

The following strains were obtained from the American Type Culture Collection, 12301 Parklawn Drive, Rockville, Maryland, U.S.A. as freeze-dried cultures:

| | |
|---|---|
| S. aureus | ATCC 6538 |
| E. coli | ATCC 8739 |
| P. aeruginosa | ATCC 9027 |

They were cultured and maintained on Tryptone Soy Agar (Oxoid CM 131), with the addition of 10% horse blood for the S. pyogenes.

To prepare the organisms as inocula for the test, slopes of this medium were streaked with the organisms and incubated at 37° C. for 24 hours. 4.5 Ml volumes of Brian-Heart Infusion Broth (Oxoid CM 225) were then inoculated with a platinum loop from the agar slope cultures and incubated for 24 hours at 37° C. The final inocula were then prepared by adding 0.1 ml aliquots of the Brain-Heart Infusion Broth cultures to 100 ml volumes of sterile physiological saline.

(b) Fungi

The following strain was obtained from the American Type Culture Collection, 12301 Parklawn Drive, Rockville, Md., U.S.A.:

| | |
|---|---|
| C. albicans | ATCC 10231 |

The following strains were obtained from the National Collection of Pathogenic Fungi at the London School of Hygiene and Tropical Medicine, Keppel Street, London WC1E7HT:

| | |
|---|---|
| C. tropicalis | NCPF 3111 |
| C. neoformans | NCPF 3184 |
| A. corymbifera | NCPF 2001 |
| A. fumigatus | NCPF 2140 |
| S. schenkii | NCPF 3182 |
| T. rubrum | NCPF 197 |
| T. mentagrophytes | NCPF 410 |
| M. canis | NCPF 351 |
| P. verrucosa | NCPF 1119 |

The two species, C. albicans and C. tropicalis, were maintained on Sabouraud-Dextrose Agar (Oxoid CM41) and cultures for the preparation of the inoculum were incubated on this agar at 37° C. for 48 hours. 4.5 Ml volumes of citric acid-phosphate buffer pH 5.5 plus Yeast-Nitrogen Base (Difco 0392-15) were then inoculated from the agar cultures and incubated at 37° C. for 48 hours. 0.1 Ml aliquots of these cultures were then added to 100 ml volumes of sterile physiological saline to give the final inocula.

The C. neoformans was also maintained on Sabouraud-Dextrose Agar (Oxoid CM 41), but in this case cultures for the preparation of the inoculum were incubated on this agar at 30° C. for 48 hours. A 4.5 ml volume of citric acid-phosphate buffer pH 5.5 plus Yeast-Nitrogen Base (Difco-0392-15) was then inoculated from the agar culture and incubated at 30° C. for 48 hours. A 0.1 ml aliquot of this culture was then added to 100 ml sterile physiological saline to give the final inoculum.

The *A. corymbifera, A. fumigatus, S. schenkii, T. rubrum, T. mentagrophytes, M. canis* and *P. verrucosa* strains were all maintained on Sabouraud-Dextrose Agar (Oxoid CM 41) by incubating for 14 days at 27° C. To prepare the inocula 30 ml volumes of Sabouraud-Liquid medium (Oxoid CM 147) were inoculated from the agar cultures and incubated at 27° C. until heavy uniform growth resulted. The mycelial growth was then broken up by shaking with glass beads.

1 Ml aliquots were removed from each of the cultures for the purpose of making viable counts and the cultures were then held at 4° C. The viable counts were made by preparing serial ten-fold dilutions of the cultures in sterile physiological saline and spreading on plates of Sabouraud-Dextrose Agar (Oxoid CM 41) which were then incubated at 27° C. for 14 days. When the viable counts had confirmed that each of the inocula contained approximately $10^6$ colony forming units (C.F.U.) per ml the cultures were withdrawn from the refrigerator and used as the inocula for the tests.

TEST PROCEDURE (a) For the test on each of the bacterial strains and each of the test and reference compounds, a series of 8 tubes containing 4.5 ml volumes of Brain-Heart Infusion Broth (Oxoid CM 225) were prepared. To 7 of these were added 0.5 ml volumes of the final solutions of the test compouns, giving final concentrations in the broths of 100, 50, 10, 5, 1.0, 0.5 and 0.1 µg/ml. To the eighth tube in each series was added 0.5 ml of the solvent used and diluted as for the preparation of the 1000 µg/ml solution of the compound. This tube was used as the growth control. The tubes were inoculated with 0.02 ml aliquots of the inocula prepared in accordance with "(a) Bacteria" above, and incubated at 37° C. for 24 hours. The tubes were then examined for evidence of bacterial growth as shown by turbidity of the medium and the lowest concentration of the test compound which prevented bacterial growth was recorded as the Minimal Inhibitory Concentration. This test procedure was carried out on two separate days.

(b) For the tests on each of the *C. albicans, C. tropicalis* and *C. neoformans* strains and each of the test and reference compounds, a series of 8 tubes containing 4.5 ml volumes of citric acid-phosphate buffer pH 5.5 plus Yeast-Nitrogen Base (Difco 0392-15) were prepared. To 7 of these were added 0.5 ml volumes of the final solutions of the test compounds, giving final concentrations in the broths of 100, 50, 10, 5, 1.0, 0.5 and 0.1 µg/ml. To the eighth tube in each series was added 0.5 ml of the solvent used and diluted as for the preparation of the 1000 µg/ml solution of the compound. This tube was used as the growth control. The tubes were then inoculated with 0.1 ml aliquots of the inocula prepared as in "(b) Fungi" above. The tubes inoculated with the *C. albicans* and *C. tropicalis* were inoculated at 37° C. for 72 hours and the tubes inoculated with the *C. neoformans* straim were incubated at 30° C. for 72 hours. (Preliminary experiments showed that this strain of *C. neoformans* grew very slowly and weakly at 37° C. but grew well at 30° C.). The tubes were then examined for evidence of growth as shown by turbidity of the medium and the lowest concentration of the test compound which prevented fungal growth was recorded as the Minimal Inhibitory Concentration. This test procedure was carried out on two separate days.

(c) For the tests on each of the remaining seven strains and each of the test and reference compounds, a series of 8 tubes containing 4.5 ml volumes of Sabouraud-Liquid Medium (Oxoid CM 147) were prepared. To 7 of these were added 0.5 ml volumes of the final solutions of the test compounds, giving final concentrations in the broths of 100, 50, 10, 5, 1.0, 0.5 and 0.1 µg/ml. To the eighth tube in each series was added 0.5 ml of the solvent used and diluted as for the preparation of the 500 µg/ml solution of the compound. This tube was used as a growth control. The tubes were then inoculated with 0.1 ml aliquots of the inocula prepared as in "(b) Fungi" above. The tubes were then incubated at 27° C. with continuous shaking for a period of one week. The tubes were then examined for evidence of growth as shown by the presence of mycelial growth in the medium and the lowest concentration of the test compound which prevented fungal growth was recorded as the Minimal Inhibitory Concentration. This test procedure was carried out on two separate days.

RESULTS

The results in terms of the duplicate Minimal Inhibitory Concentrations of each of the test compounds against each of the microorganisms are shown in the following tables:

TABLE 1

| Compound of Example No. | Antibacterial Activity: Minimum Inhibitory Concentration (µg/ml) | | | | | | | | | |
|---|---|---|---|---|---|---|---|---|---|---|
| | S. aureus | | S. pyogenes | | E. coli | | P. mirabilis | | P. aerugisosa | |
| | Day 1 | Day 2 | Day 1 | Day 2 | Day 1 | Day 2 | Day 1 | Day 2 | Day 1 | Day 2 |
| 2 | 0.5 | 0.5 | 0.5 | 0.5 | 10 | 5 | 10 | 10 | 10 | 5 |
| 1 | 5 | 5 | 1 | 0.5 | 50 | 100 | 100 | 100 | 50 | 10 |
| 7 | 0.5 | 0.5 | 0.5 | 0.5 | 10 | 5 | 10 | 50 | 50 | 10 |
| 6-C | 0.5 | 0.5 | 0.5 | 0.5 | 10 | 10 | 10 | 50 | 5 | 10 |
| 3-D | 0.5 | 0.5 | 0.5 | 0.5 | 10 | 5 | 10 | 50 | 50 | 10 |
| 3-E | 1 | 1 | 5 | 5 | 50 | 50 | 100 | 100 | 50 | 50 |
| 3-G | 0.5 | 0.5 | 0.5 | 0.5 | 10 | 10 | 50 | 50 | 10 | 10 |
| 6-E | 0.5 | 0.5 | 0.5 | 0.5 | 10 | 10 | 50 | 50 | 5 | 5 |
| 8-A | 1 | 0.5 | 5 | 5 | 50 | 50 | 100 | 100 | 50 | 50 |
| 6-B | 0.5 | 0.5 | 0.5 | 0.5 | 10 | 5 | 50 | 50 | 10 | 10 |
| 9 | 0.5 | 0.5 | 0.5 | 0.5 | 50 | 10 | 10 | 10 | 10 | 10 |
| 6-D | 1 | 0.5 | 0.5 | 1 | 50 | 100 | 50 | 50 | 100 | 50 |
| Gentamicin | 0.5 | 0.5 | 0.5 | 0.5 | 10 | 10 | 5 | 5 | 1 | 1 |

Table 2

| Compound of Example No. | Antimycotic activity: Minimum Inhibitory Concentrations (µg/ml) | | | | | |
|---|---|---|---|---|---|---|
| | C. albicans | | C. tropicalis | | C. neoformans | |
| | Day 1 | Day 2 | Day 1 | Day 2 | Day 1 | Day 2 |
| 2 | 1 | 1 | 1 | 0.5 | 0.5 | 0.5 |

Table 2-continued

| Compound of Example No. | Antimycotic activity: Minimum Inhibitory Concentrations (μg/ml) | | | | | |
|---|---|---|---|---|---|---|
| | C. albicans | | C. tropicalis | | C. neoformans | |
| | Day 1 | Day 2 | Day 1 | Day 2 | Day 1 | Day 2 |
| 1 | 10 | 50 | 5 | 5 | 0.5 | 0.5 |
| 7 | 5 | 1 | 0.5 | 0.5 | 1 | 0.5 |
| 6-C | 5 | 5 | 5 | 1 | 1 | 1 |
| 3-D | 1 | 1 | 0.5 | 0.5 | 5 | 1 |
| 3-E | 50 | 50 | 5 | 1 | 1 | 5 |
| 3-G | 5 | 5 | 0.5 | 0.5 | 1 | 1 |
| 6-E | 1 | 5 | 5 | 1 | 0.5 | 0.5 |
| 8-A | 10 | 50 | 5 | 5 | 5 | 1 |
| 6-B | 5 | 5 | 1 | 1 | 1 | 1 |
| 9 | 5 | 10 | 5 | 1 | 1 | 0.5 |
| 6-D | 10 | 5 | 5 | 5 | 0.5 | 0.5 |
| Amphotericin B | 1 | 1 | 1 | 1 | 1 | 0.5 | or to be protected against attack by fungus or bacterium can be treated with the subject compounds and the compositions thereof by dusting, sprinkling, spraying, brushing, dipping, smearing, impregnating or other suitable means.

A particularly useful form of utilizing the subject compounds (I) is in the form of aerosols. For this purpose, the active component is dissolved or dispersed, if necessary, with the aid of suitable inert solvents as carrier liquids, such as difluorodichloromethane, which at atmospheric pressure boils at a termperature lower than room temperature, or in other volatile solvents. In this way, solutions under pressure are obtained which, when sprayed, yield aerosols which are particularly suitable for controlling or combatting fungi and bacteria, e.g., in closed chambers and storage rooms, and for application to vegetation for eradicating or for preventing infections by fungi or bacteria.

TABLE 3

| Compound of Example No. | Antifungal activity: Minimum Inhibitory Concentration (μg/ml) | | | | | | | | | | | | | | |
|---|---|---|---|---|---|---|---|---|---|---|---|---|---|---|---|
| | A. corymbifera | | A. fumigatus | | S. schenkii | | T. rubrum | | T. mentagrophytes | | M. canis | | P. verrucoso | |
| | Day 1 | Day 2 | Day 1 | Day 2 | Day 1 | Day 2 | Day 1 | Day 2 | Day 1 | Day 2 | Day 1 | Day 2 | Day 1 | Day 2 |
| 2 | 50 | 50 | 10 | 5 | 10 | 10 | 5 | 5 | 1 | 5 | 10 | 5 | 5 | 10 |
| 1 | >100 | >100 | 100 | >100 | 50 | 10 | 10 | 10 | 50 | 50 | 5 | 10 | 5 | 5 |
| 7 | 5 | 5 | 10 | 50 | 5 | 5 | 1 | 1 | 1 | 5 | 5 | 10 | 5 | 5 |
| 6-C | 10 | 10 | 5 | 5 | 5 | 5 | 5 | 5 | 5 | 5 | 5 | 5 | 5 | 5 |
| 3-D | 10 | 5 | 50 | 10 | 5 | 10 | 1 | 1 | 1 | 1 | 5 | 5 | 5 | 5 |
| 3-E | 100 | 100 | 50 | 10 | 50 | 10 | 5 | 5 | 1 | 5 | 10 | 10 | 5 | 10 |
| 3-G | 10 | 10 | 50 | 50 | 5 | 10 | 1 | 5 | 1 | 5 | 10 | 5 | 5 | 5 |
| 6-E | 10 | 50 | 10 | 5 | 5 | 1 | .5 | 5 | 5 | 5 | 1 | 5 | 5 | 5 |
| 8-A | 100 | 100 | 100 | 100 | 10 | 10 | 5 | 10 | 5 | 5 | 5 | 1 | 10 | 10 |
| 6-B | 10 | 10 | 5 | 5 | 1 | 1 | 5 | 1 | 1 | 1 | 5 | 5 | 5 | 5 |
| 9 | 10 | 10 | 5 | 10 | 5 | 5 | 5 | 5 | 5 | 5 | 5 | 5 | 5 | 10 |
| 6-D | 50 | 50 | 50 | 50 | 5 | 5 | 10 | 10 | 10 | 10 | 10 | 5 | 10 | 10 |
| Amphotericin B | 5 | 5 | 5 | 5 | 50 | 50 | 50 | 50 | 50 | 50 | 1 | 1 | 10 | 10 |

In view of their antibacterial and antifungal activities, the subject compounds (I) are useful antimicrobial agents which may be formulated with suitable inert carriers into usable antimicrobial compositions, for example, as sterilizing solutions, disinfectants and the like.

Advantageously, many of the formula (I) compounds demonstrate a high degree of water solubility and lend themselves to the preparation of aqueous concentrates. In practice, the aqueous concentrates may be applied directly to the subject to be treated or may be further diluted with a water miscible solvent to a desired concentration prior to use.

Emulsifiable concentrates are prepared by dissolving from 15 to 95 percent of the formula (I) compound in 85 to 5 percent of a water miscible solvent, such as water itself or another polar water miscible solvent, such as 2-methoxy ethanol, methanol, propylene glycol, diethylene glycol, diethylene glycol monoethyl ether, formamide and dimethylformamide. Such concentrates are suitable for application as liquid sprays as such or in combination with a suitable diluent.

Performance is generally improved by adding a surfactant or blend of surfactants. Conventional anionic, cationic and non-ionic surfactants may be employed, such as described in U.S. Pat. No. 3,966,954.

Other formulations which may be used to advantage with the subject compounds (I) include dusts, dust concentrates and wettable powders, such as is also described in said patent.

The subject compounds (I) and compositions thereof can be applied by conventional methods. For example, a fungus or bacterial growth or a material to be treated When the subject compounds (I) are employed in combination with suitable carriers, e.g., in solution, suspension, dust, powder, ointment, emulsion, and the like forms, a high activity over a very high range of dilution is observed. For example, concentrations of the active ingredient ranging from at least 0.01 percent and, preferably, from about 0.1 to about 15 percent by weight, based on the weight of compositions employed, have been found effective in combatting fungi or bacteria. Of course, higher or lower concentrations may also be employed as warranted by the particular situation. If desired, other compounds having, for example, arachnicidal, insecticidal, oricidal, fungicidal and/or bacterial effects may be included in the compositions.

In addition to their antifungal and antibacterial properties, the subject compounds (I) also possess algicidic activity which makes them suitable for such usage wherever water bodies are subject to infestation, e.g., in a swimming pool, with algae, including green algae, blue algae and diatoms. The activity and method of usage of the subject compounds is similar to that of the known algicide, Hyamine 3500. The addition of from about 0.001 to about 1.0 percent by weight of the subject compounds to water is generally quite sufficient for protection against algae. In practical usage, it is evident that aqueous concentrates with higher percentages, e.g., 10–90% of the subject compounds may be formulated for appropriate dilution upon usage.

A comparison of the algicidic activity of the preferred compound, 1-hexadecyl-2,3,5-trimethylpyrazolium methosulfate, with said standard is shown in Table 4.

yields 1-tetra-decyl-2,3,5-tri-methyl-pyrazolium methosulfate; m.p. 89.5°–91° C.

TABLE 4

| Algae (diatoms, green and blue algae) Compound | Dosage mg/l water | % algicidal activity ... weeks after treatment | | | | | | |
|---|---|---|---|---|---|---|---|---|
| | | 1 | 2 | 3 | 4 | 5 | 6 | x̄ |
| Hyamine 3500 (Standard algicide) [$C_nH_{n+1}$–N(CH$_3$)(CH$_3$)–CH$_2$–C$_6$H$_5$]$^+$ Cl$^-$ | 4 | 100 | 100 | 100 | 99 | 97 | 95 | 98 |
| | 2 | 100 | 100 | 100 | 97 | 88 | 80 | 94 |
| | 1 | 100 | 99 | 93 | 88 | 76 | 68 | 87 |
| Test Compound (pyrazolium structure with CH$_3$, C$_{16}$H$_{33}$, CH$_3$ CH$_3$SO$_4^-$) | 4 | 100 | 100 | 100 | 100 | 100 | 100 | 100 |
| | 2 | 100 | 100 | 100 | 100 | 100 | 98 | 99 |
| | 1 | 100 | 100 | 100 | 96 | 93 | 88 | 96 |
| | | % water turbidity caused by growth of algae | | | | | | |
| Untreated | — | 24 | 42 | 57 | 62 | 67 | 75 | |

Results given above are mean values from 2 replicates of trial.

Test conditions: Severe with high infection pressure after artificial algae inoculation in 350 liter concrete pools under outdoor conditions.
Stains included: Green algae: Chlorella, Zygnema, Hormidium + Scenedesmus species
 Blue algae: Phormidium species
 Diatoms: Nitzschea pallea
Water temperature: Day: 21° C., night: 18°–20° C.

In view of the foregoing, it is evident that the instant invention provides an effective method of combatting the growth of microorganisms by use of an effective antimicrobial amount of the subject compounds (I) in admixture with an inert carrier.

The following examples are intended to illustrate but not to limit the scope of the present invention.

EXAMPLE 1

A mixture of 39.7 g (0.15 mol) of 3,5-dimethyl-1-dodecyl-pyrazole (described in CA 63, 8339 g); 18.9 g (0.15 mol) of dimethyl sulfate and 90 ml of ethyl acetate is refluxed for 6 hrs. After cooling, the resultant crystalate is filtered off and recrystallized from 80 ml o ethyl acetate. After filtration and drying in vacuum at 50° C. a yield of about 50.8 g of 1-dodecyl-2,3,5-trimethyl-pyrazolium methosulfate is obtained; m.p. 85°–86° C.

EXAMPLE 2

A mixture of 15.0 g (0.0468 mol) of 1-hexadecyl-3,5-dimethyl-pyrazole (CA 63, 8339 e-g); 6.1 g (0.0484 mol) of dimethyl sulfate and 25 ml of ethyl acetate is refluxed for 8 hrs, filtered while hot, and left standing overnight (about 16 hrs.). The crystal is then filtered off, washed with ethyl acetate and dried (at 50° C./12 Torr) to yield about 17.2 g of 1-hexadecyl-2,3,5-trimethyl-pyrazolium methosulfate; m.p. 95°–96° C.

EXAMPLE 3

In a similar way as described in Examples 1 and 2, except that equivalent amounts of reactants are used, the following pyrazolium salts are obtained by quaternization of the identified 1-R-3-R$_2$-5-R$_3$-pyrazole precursors of formula (II):

A. Reaction of 3,5-dimethyl-1-undecyl-pyrazole (b.p.: 107°–109° C./0.01 Torr) with dimethyl sulfate yields 2,3,5-trimethyl-1-undecylpyrazolium methosulfate; m.p. 86°–87° C.

B. Reaction of 3,5-dimethyl-1-tetradecyl-pyrazole (b.p.: 132°–133.5° C./0.01 Torr) with dimethyl sulfate C. Reaction of 1-octadecyl-3,5-dimethyl-pyrazole (CA 63, 8339 e-g) with dimethyl sulfate yields 1-octadecyl-2,3,5-trimethyl-pyrazolium methosulfate; m.p. 95°–97° C.

D. Reaction of 1-hexadecyl-pyrazole (b.p.: 149°/151° C./0.03 Torr) with dimethyl sulfate yields 1-hexadecyl-2-methyl-pyrazolium methosulfate; m.p. 63°–65° C.

E. Reaction of 1-dodecyl-pyrazole (b.p.: 107.5°–109° C./0.06 Torr) with dimethyl sulfate yields 1-dodecyl-2-methy-pyrazolium methosulfate (a non-crystallizing oil). The identity was demonstrated by microanalysis.

| N calculated 7.72% | found 7.78% |
|---|---|
| S calculated 8.84% | found 9.01% |

F. Reaction of 1-tetradecyl-pyrazole (b.p.: 125°–128° C./0.06 Torr) with diethyl sulfate yields 2-ethyl-1-tetradecyl-pyrazolium ethosulfate; m.p. 20°–22° C.

G. Reaction of 1-tetradecyl-pyrazole with dimethyl sulfate yields 2-methyl-1-tetradecyl-pyrazolium methosulfate; m.p. 52°–54° C.

H. Reaction of 3,5-dimethyl-1-tetradecyl-pyrazole with diethyl sulfate yields 2-ethyl-3,5-dimethyl-1-tetradecyl-pyrazolium ethosulfate (a poorly crystallizing substance); m.p. 18°–20° C.

I. Reaction of 1-hexadecyl-3,5-dimethyl-pyrazole with diethyl sulfate yields 2-ethyl-1-hexadecyl-3,5-dimethyl-pyrazolium ethosulfate; m.p. 49°–51° C.

EXAMPLE 4

A. A mixture of 16. g (0.05 mol) of 1-hexadecyl-3,5-dimethylpyrazole and 50 ml of sulfolane is cooled down to −30° C. in a rotary autoclave and 9 g (0.18 mol) of liquid methyl-chloride cooled down to −40° C. are added. Upon sealing the autoclave, the reaction mixture is heated to 120° C. and kept at this temperature for 60 hrs. After cooling, the sulfolane is distilled off under high vacuum. 50 Ml of ether are added to the residue and the mixture shaken thoroughly. The crystalate is then filtered off and recrystallized first from 100 ml of acetone and then from 60 ml of acetone, filtered off, and vacuum dried at 40° C./12 Torr to yield about 10.1 g of 1-hexadecyl-2,3,5-trimethyl-pyrazolium chloride; m.p. 92°–94° C. The same compound is obtained by appropriate anion exchange of the product obtained in Example I.

B. In the same way as described in Example 4-A, reaction of 1-hexadecyl-3,5-dimethyl-pyrazole with ethyl bromide yields 2-ethyl-1-hexadecyl-3,5-dimethyl-pyrazolium bromide; m.p. 97°–101° C.

C. When 1-hexadecyl-2,3,5-trimethyl-pyrazole methosulfate is treated with a strongly basic ion exchanger (e.g., Amberlite IRA-401), the corresponding quaternary base is released. By adding phosphoric acid, 1-hexadecyl-2,3,5-trimethyl-pyrazolium phosphate is obtained; m.p. 96°–100° C.

EXAMPLE 5

A mixture of 48.1 g (0.150 mol) of 3,5-dimethyl-1-hexadecyl-pyrazole, 25.6 g (0.150 mol) of benzyl bromide and 200 ml of sulfolane is stirred and heated to 100° C., and then kept at this temperature for 11 hrs. The reaction mixture is allowed to cool down overnight. It is then stirred and 100 ml of ethyl acetate is added. The crystalate is filtered off, washed with ethyl acetate, and vacuum dried at 50° C./12 Torr to yield about 36.3 g of 2-benzyl-3,5-dimethyl-1-hexadecyl-pyrazolium bromide; m.p. 166°–167° C.

EXAMPLE 6

By following the procedure of Example 5, except that equivalent quantities of the indicated reactants are employed, the following products are obtained:

A. Reaction of 3,5-dimethyl-1-octadecyl-pyrazole with benzyl bromide yields 2-benzyl-3,5-dimethyl-1-octadecyl-pyrazolium bromide; m.p. 165.5°–167.5° C.

B. Reaction of 3,5-dimethyl-1-dodecyl-pyrazole with 2,4-dichlorobenzylbromide yields 2-(2,4-dichlorobenzyl)-3,5-dimethyl-1-dodecyl-pyrazolium bromide; m.p. 139°–140.5° C.

C. Reaction of 3,5-dimethyl-1-hexadecyl-pyrazole with toluene-4-sulfonic acid-methyl ester yields 1-hexadecyl-2,3,5-trimethylpyrazolium p-toluene sulfonate; m.p. 113°–114° C.

D. Reaction of 3,5-dimethyl-1-tetradecyl-pyrazole with 4-nitrobenzyl bromide yields 3,5-dimethyl-2(4-nitrobenzyl)-1-tetradecyl-pyrazolium bromide; m.p. 159°–161° C.

E. Reaction of 3,5-dimethyl-1-dodecyl-pyrazole with p-chlorobenzyl bromide yields 2-(p-chlorobenzyl)-3,5-dimethyl-1-dodecyl-pyrazolium bromide; m.p. 166.5°–167.5° C.

EXAMPLE 7

A mixture of 50 g (0.156 mol) of 3,5-dimethyl-1-hexadecylpyrazole, 200 ml of sulfolane and 19 g (0.156 mol) of allyl bromide is stirred and kept at a temperature of 80° C. for 24 hrs. The reaction mixture is allowed to cool and 100 ml of ether are added. The mixture is stirred for another 2 hrs and the crystalate is then filtered off, washed with ether, and vacuum dired at 40° C./12 Torr. Recrystallization from 200 ml of ethyl acetate yields 39.6 g of 2-allyl-3,5-dimethyl-1-hexadecyl-pyrazolium bromide; m.p. 99°–100° C.

EXAMPLE 8

A. A mixture of 12.5 g (0.05 mol) of 1-dodecyl-3(5)-methyl-pyrazole (b.p.: 110°–112° C./0.05 Torr), 30 ml of ethyl acetate and 6.3 g (0.05 mol) of dimethyl sulfate is stirred, heated, and refluxed for 10 hrs. The reaction solution is completely vacuum concentrated at 40° C./12 Torr. The resultant oil that partly crystallizes upon cooling is dissolved in 50 ml of water. The aqueous solution is extracted three times with 50 ml each of chloroform. The chloroform solutions are collected and dried over $Na_2SO_4$ and complete vacuum concentrated at 40° C./12 Torr to yield 13.8 g of an oil consisting of a mixture of 2,3-dimethyl-1-dodecyl-pyrazolium methosulfate and 2,5-dimethyl-1-dodecyl-pyrazolium methosulfate, which can be denoted as 2,3(5)-dimethyl-1-dodecyl-pyrazolium methosulfate.

| N calculated 7.44% | found 7.35% |
| --- | --- |
| S calculated 8.52% | found 8.45% |

Reaction of 3-methyl-pyrazole with alkyl halides yields a mixture of 1,3 and 1,5 isomers which, when quaternized, results in an oily mixture of the quaternary 1,2,3- and 1,2,5-isomers. Such oily mixtures generally crystallize partly when left standing for a prolonged period of time. In order to obtain uniform samples it is therefore necessary to slightly heat such mixture before samples are taken for analyses or tests.

B. In the same way as described in Example 8-A the following compounds are prepared:

Reaction of 3(5)-methyl-1-tetradecyl-pyrazole (b.p.: 133°–135° C./0.07 Torr) with dimethyl sulfate yields a mixture of 2,3-dimethyl- and 2,5-dimethyl-1-tetradecyl-pyrazolium methosulfate, which can be denoted as 2,3(5)-dimethyl-1-tetradecyl-pyrazolium methosulfate. This mixture crystallizes up to about 50%.

| N calculated 6.92% | found 6.85% |
| --- | --- |
| S calculated 7.92% | found 7.99% |

EXAMPLE 9

A mixture of 16.0 (0.0522 mol) of 1-hexadecyl-3(5)-methyl-pyrazole (b.p.: 159°–164° C./0.05 Torr), 6.6 g (0.527 mol) of dimethyl sulfate and 30 ml of ethyl acetate is refluxed for 10 hrs. The product, which crystallized upon standing overnight, is filtered off and vacuum driedat 30° C./12 Torr to yield about 20.1 g of 2,3(5)-dimethyl-1-hexadecyl-pyrazolium methosulfate; m.p. 63°–65° C.

EXAMPLE 10

A. The procedure of Example 2 is followed except that an equivalent quantity of 1-decyl-3,5-dimethyl-pyrazole is used as the starting material to be quaternized to yield as the final product, 1-decyl-2,3,5-trimethyl-pyrazolium methosulfate; m.p. 74°–76° C.

B. By following the procedure of Example 5, except that an equivalent quantity of 1-decyl-3,5-dimethyl pyrazole is used as the starting material, there is obtained as the end product, 2-benzyl-1-decyl-3,5-dimethyl-pyrazolium bromide; m.p. 151°–153° C. The precursor, 1-decyl-3,5-dimethylpyrazole, can be prepared by one of the methods heretofore indicated; b.p. 176°–179° C./12 Torr.

We claim:

1. A quaternary pyrazole having the formula:

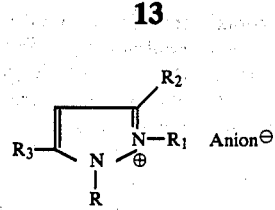

wherein:
R is an alkyl having from 10 to 18 carbons with at least 10 carbons in its longest chain;
$R_1$ is a member selected from the group consisting of lower alkyl, $C_3$-$C_5$ alkenyl, benzyl, nitrobenzyl, halobenzyl and dihalobenzyl;
$R_2$ is a member selected from the group consisting of hydrogen and methyl; and
$R_3$ is a member selected from the group consisting of hydrogen and methyl.

2. The quaternary pyrazole of claim 1 wherein R is dodecyl.
3. The quaternary pyrazole of claim 1 wherein R is tetradecyl.
4. The quaternary pyrazole of claim 1 wherein R is hexadecyl.
5. 1-Dodecyl-2,3,5-trimethyl-pyrazolium methosulfate.
6. 1-Hexadecyl-2,3,5-trimethyl-pyrazolium methosulfate.
7. 1-Hexadecyl-2-methyl-pyrazolium methosulfate.
8. 1-Dodecyl-2-methyl-pyrazolium methosulfate.
9. 2-Methyl-1-tetradecyl-pyrazolium methosulfate.
10. 2-(2,4-Dichlorobenzyl)-3,5-dimethyl-1-dodecyl-pyrazolium bromide.
11. 1-Hexadecyl-2,3,5-trimethyl-pyrazolium p-toluene sulfonate.
12. 3,5-Dimethyl-2-(4-nitrobenzyl)-1-tetradecyl-pyrazolium bromide.
13. 2-(p-Chlorobenzyl)-3,5-dimethyl-1-dimethyl-1-dodecyl-pyrazolium bromide.
14. 2-Allyl-3,5-dimethyl-1-hexadecyl-pyrazolium bromide.
15. 2,3(5)-Dimethyl-1-dodecyl-pyrazolium methosulfate.
16. 2,3(5)-Dimethyl-1-hexadecyl-pyrazolium methosulfate.
17. 2-Benzyl-1-decyl-3,5-dimethyl-pyrazolium bromide.
18. An antimicrobial composition comprising an effective amount of a quaternary pyrazole in admixture with an inert carrier, said quaternary pyrazole having the formula:

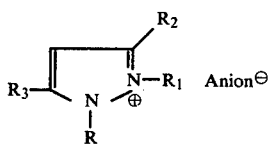

wherein:
R is an alkyl having from 10 to 18 carbons with at least 10 carbons in its longest chain;
$R_1$ is a member selected from the group consisting of lower alkyl, $C_3$-$C_5$ alkenyl, benzyl, nitrobenzyl, halobenzyl and dihalobenzyl;
$R_2$ is a member selected from the group consisting of hydrogen and methyl; and
$R_3$ is a member selected from the group consisting of hydrogen and methyl.

19. An antimicrobial composition comprising an effective amount of 1-hexadecyl-2,3,5-trimethyl pyrazolium methosulfate in admixture with an inert carrier.
20. An antimicrobial composition comprising an effective amount of 1-hexadecyl-2-methyl-pyrazolium methosulfate in admixture with an inert carrier.
21. An antimicrobial composition comprising an effective amount of 2-methyl-1-tetradecyl-pyrazolium methosulfate in admixture with an inert carrier.
22. An antimicrobial composition comprising an effective amount of 2-(2,4-dichlorobenzyl)-3,5-dimethyl-1-dodecyl-pyrazolium bromide in admixture with an inert carrier.
23. An antimicrobial composition comprising an effective amount of 1-hexadecyl-2,3,5-trimethyl-pyrazolium p-toluene sulfonate in admixture with an inert carrier.
24. An antimicrobial composition comprising an effective amount of 2-(p-chlorobenzyl)-3,5-dimethyl-1-dodecyl-pyrazolium bromide in admixture with an inert carrier.
25. An antimicrobial composition comprising an effective amount of 2-allyl-3,5-dimethyl-1-hexadecyl-pyrazolium bromide in admixture with an inert carrier.
26. An antimicrobial composition comprising an effective amount of 2,3(5)-dimethyl-1-hexadecyl-pyrazolium methosulfate in admixture with an inert carrier.
27. A method of combatting microorganisms which comprises contacting said microorganisms with an effective antimicrobial amount of a quaternary pyrazole having the formula:

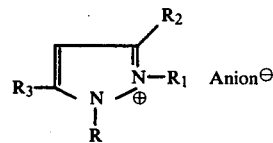

wherein:
R is an alkyl having from 10 to 18 carbons with at least 10 carbons in its longest chain;
$R_1$ is a member selected from the group consisting of lower alkyl, $C_3$-$C_5$ alkenyl, benzyl, nitrobenzyl, halobenzyl and dihalobenzyl;
$R_2$ is a member selected from the group consisting of hydrogen and methyl; and
$R_3$ is a member selected from the group consisting of hydrogen and methyl.

28. A method of combatting microorganisms which comprises contacting said microorganisms with an effective antimicrobial amount of 1-hexadecyl-2,3,5-trimethyl pyrazolium methosulfate.
29. A method of combatting microorganisms which comprises contacting said microorganisms with an effective antimicrobial amount of 1-hexadecyl-2-methyl-pyrazolium methosulfate.
30. A method of combatting microorganisms which comprises contacting said microorganisms with an effective antimicrobial amount of 2-methyl-1-tetradecyl-pyrazolium methosulfate.
31. A method of combatting microorganisms which comprises contacting said microorganisms with an effective antimicrobial amount of 2-(2,4-dichlorobenzyl)-3,5-dimethyl-1-dodecyl-pyrazolium bromide.

32. A method of combatting microorganisms which comprises contacting said microorganisms with an effective antimicrobial amount of 1-hexadecyl-2,3,5-trimethyl-pyrazolium p-toluene sulfonate.

33. A method of combatting microorganisms which comprises contacting said microorganisms with an effective antimicrobial amount 2-(p-chlorobenzyl)-3,5-dimethyl-1-dodecyl-pyrazolium bromide.

34. A method of combatting microorganisms which comprises contacting said microorganisms with an effective antimicrobial amount 2-allyl-3,5-dimethyl-1-hexadecyl-pyrazolium bromide.

35. A method of combatting microorganisms which comprises contacting said microorganisms with an effective antimicrobial amount of 2,3(5)-dimethyl-1-hexadecyl-pyrazolium methosulfate.

* * * * *